United States Patent [19]

Eguchi et al.

[11] Patent Number: 4,650,667
[45] Date of Patent: Mar. 17, 1987

[54] GAS-EMITTING BATH ADDITIVE COMPOSITION

[75] Inventors: Yasuteru Eguchi, Utsunomiya; Hidenori Yorozu, Mashikomachi; Eiji Iijima, Utsunomiya, all of Japan

[73] Assignee: Kao Corporation, Tokyo, Japan

[21] Appl. No.: 577,717

[22] Filed: Feb. 7, 1984

[51] Int. Cl.$^4$ .................................................. A61L 9/04
[52] U.S. Cl. ...................................... 424/44; 514/957; 514/958; 514/959; 514/970
[58] Field of Search .................. 424/44; 514/957, 958, 514/959, 970

[56] References Cited

U.S. PATENT DOCUMENTS

| | | | |
|---|---|---|---|
| 3,506,756 | 4/1970 | Hoss | 424/44 |
| 3,584,099 | 6/1971 | Hoss | 424/44 |

FOREIGN PATENT DOCUMENTS

| | | | |
|---|---|---|---|
| 55-7246 | 1/1980 | Japan | 424/44 |
| 7700844 | 7/1978 | Netherlands | 424/44 |
| 1292820 | 10/1972 | United Kingdom | 424/44 |

OTHER PUBLICATIONS

Gregory, *Uses & Applns. of Chemicals & Related Mat'ls.*, pp. 558 (1939).

*Primary Examiner*—Leonard Schenkman
*Assistant Examiner*—F. Abramson
*Attorney, Agent, or Firm*—Oblon, Fisher, Spivak, McClelland & Maier

[57] ABSTRACT

Gas-emitting bath additive compositions are stably preserved over a long term. They comprise a carbonate, an organic acid, and a stabilizer which is selected from magnesium oxide, sodium aluminate and a mixture thereof. Magnesium oxide and sodium aluminate are effective to improve the preservation stability of bath additives when used in an amount of 0.1 to 1.5 wt % of the total composition.

14 Claims, No Drawings

GAS-EMITTING BATH ADDITIVE COMPOSITION

BACKGROUND OF THE INVENTION (i) Field of the Invention

This invention relates to gas-emitting bath additive compositions which are stably preserved over a long term.

(ii) Description of the Prior Art

Bath additives are usually made of mixtures of inorganic salts or materials such as Glauber's salt, borax, sulfur, sodium chloride, carbonates and the like, admixed with perfumes, colorants, plant extracts, organic acids and the like. These additives serve to impart agreeable fragrance and color to a hot bath and also to give a proper impetus to skin, thus promoting the circulation of blood and leading to recruitment and promotion of metabolism. Among these bath additives, there are known gas-emitting bath additives comprising combinations of carbonates and organic acids. This type of gas-emitting bath additive allows carbon dioxide gas to be generated or emitted in or throughout a hot bath, producing the effect of permitting one to relax and refresh while enjoying the bath.

However, even though anhydrous carbonates and anhydrous organic acids are used in these gas-emitting bath additives, they are so unstable as to permit reaction therebetween even by presence of a very small amount of moisture or water, causing carbon dioxide to be generated at the time when not required. Accordingly, even when such gas-emitting bath additives are tightly packed in container and preserved over a long term, such a container is expanded by the action of carbon dioxide gas generated. This results in poor appearance of the container and a lowering of commercial value, with the attendant disadvantage that the satisfactory gas-emitting effect cannot be achieved because of a lowering of gas-emitting ability.

In order to overcome the disadvantages, attempts have been made, without practical success, to use moisture absorbents such as anhydrous sodium sulfate, starch and the like.

SUMMARY OF THE INVENTION

We have now made intensive studies on gas-emitting bath additives and, as a result, found that use of magnesium oxide and/or sodium aluminate leads to gas-emitting bath additives which are stable with respect to preservation.

According to the present invention, there is provided a gas-emitting bath additive composition which comprises a mixture of a carbonate and an organic acid, and a stabilizer for the mixture selected from the group consisting of magnesium oxide, sodium aluminate and a mixture thereof.

DETAILED DESCRIPTION OF THE INVENTION AND PREFERRED EMBODIMENTS

The carbonates used in the gas-emitting bath additive of the present invention include, for example, dried sodium hydrogencarbonate, sodium carbonate, sodium sesquicarbonate, potassium carbonate, potassium hydrogencarbonate, ammonium carbonate and the like. Of these, sodium hydrogencarbonate and sodium carbonate are preferred. The content of the carbonate is in the range of 5–80 wt %, preferably 10–50 wt %, of the total weight of the composition.

The organic acids are, for example, dried citric acid, tartaric acid, malic acid, malonic acid, pyridonecarboxilic acid, succinic acid, fumaric acid, phosphoric acid, sodium citrate, sodium succinate, sodium fumarate, sodium phosphate and the like. These acids are properly used depending on the desired effect of the bath additive. The amount of the organic acid is in the range of 10–300 wt %, preferably 30–150 wt %, of the weight of the carbonate present in the bath composition.

Upon charge of a bath additive comprising a carbonate and an organic acid into a hot bath, carbon dioxide gas generates by reaction therebetween. The effect of the generated carbon dioxide gas depends on the pH of a hot bath. When a hot bath is acidic, carbon dioxide gas exists as $CO_2$ molecules, showing the action of promoting the blood circulation. On the contrary, when a hot bath has a pH on an alkaline side, such an effect as mentioned above is not developed because carbon dioxide gas is present as $CO_3^{2-}$ or $HCO_3^-$. From this, it is favorable to control a mixing ratio of a carbonate and an organic acid in such a way that a hot bath is weakly acidic when the gas-emitting bath additive is charged thereinto, e.g. an aqueous solution of 0.01 wt % of the bath additive has a pH of 5–7. The weakly acidic hot bath is close to the skin in pH and gives a favorable influence on the skin. In order to attain the weak acidity, the content of organic acids are preferably as follows: it is in the range of 20–150 wt % of carbonate (calculated as sodium hydrogencarbonate) for succinic acid or fumaric acid, in the range of 40–300 wt % of carbonate for sodium succinate, and in the range of 30–250 wt % of carbonate for sodium fumarate.

On the other hand, in case where the bath additive of the present invention is expected to emit or generate carbon dioxide gas without expecting any pharmacological effect, the two ingredients may be mixed to have a neutral to weakly alkaline pH range. In the case, it is preferable that a mixing ratio of an organic acid to a carbonate is smaller than in the abovementioned case.

In the practice of the invention, magnesium oxide and/or sodium aluminate which is used as a stabilizer is used in an amount ranging 0.5–15 wt %, preferably 0.5–10 wt %, based on the total weight of the composition. Amounts less than 0.1 wt % are unsatisfactory in the stabilizing effect, whereas amounts exceeding 15 wt % are unfavorable because several troubles are produced, e.g. the hot bath becomes very cloudy or floating matters are produced or soap does scarcely lather.

The gas-emitting bath additive composition of the invention may further comprise, aside from the above-indicated ingredients, sulfates such as sodium sulfate, magnesium sulfate, zinc sulfate and the like, chlorides such as sodium chloride, and the like, by which there are obtained effects of hot springs such as Glauber's salt hot spring, sulfate hot spring, salt hot spring and the like. The amounts of these compounds are, in combination, in the range of 30–500 wt %, preferably 50–200 wt %, of the total weight of a carbonate, an organic acid and a stabilizer used.

The gas-emitting bath additive of the invention may further comprise perfumes, colorants and, if desired, vitamins, effective components from hot spring, proteinases, seaweed extracts, sodium aluginate, lanolin, silicones, amphoteric active agents, and crude drugs or extracts thereof.

The gas-emitting bath additive may be formed as powder, granules, crystals, tablets and the like. Among them, tablets are the most preferable from the viewpoint of gas absorption. For the preparation, any known excipients, binders disintegrators, lubricants and the like may be added as usual. The prepared or shaped gas-emitting bath additive may be packed in a packaging material substantially impermeable to water, e.g. in an aluminum laminate film, for a single usage. Alternatively, such additive may be wholly placed in a sealed container for commercial purposes.

As will be appreciated from the foregoing, the gas-emitting bath additive of the invention is stable over a long term and readily dissolves in a hot bath, thus being easy in handling. In addition, it generates or emits gas in an adequate degree, which serves to refresh or relax one in the bath. The bath additive which is controlled to be weakly acidic has the effect of promoting the circulation of blood by its vasodilating action.

The present invention is illustrated by way of example, in which parts are by weight.

EXAMPLE 1

Fifty parts of sodium hydrogencarbonate, 50 parts by weight of citric acid, 1 part of magnesium oxide, 1 part of a perfume, and a suitable amount of a colorant were placed in a powder mixer and mixed sufficiently. The mixture was shaped in a tableting machine to obtain tablets having a diameter of 3 cm and a thickness of 1 cm. The tablets were tightly packed in an aluminum laminate film and preserved at a temperature of 40° C. in a relative humidity of 75% for 6 months. The packed tablets suffered no change. Upon charge of the tablets into a hot bath, it could generate gas in a suitable degree, giving a massothreapeutical effect on the skin and permitting one to be refreshed.

EXAMPLE 2

Seventy parts of sodium hydrogencarbonate, 30 parts of tartaric acid, 1 part of magnesium oxide, 1 part of a perfume and a suitable amount of a colorant were placed in a powder mixer and sufficiently mixed to give a powdery gas-emitting bath additive. This powder was packed in the same manner as in Example 1 and preserved at a temperature of 40° C. in a relatively humidity of 75% for 6 months. The packed powder suffered no change. When the powder was charged into a hot bath, bubbles were generated intensely, giving a massothreapeutical effect on the skin and permitting one to be refreshed.

EXAMPLE 3

Seventy parts of sodium carbonate, 30 parts of citric acid, 5 part of sodium aluminate, 2 part of a perfume, and a suitable amount of a colorant were used and treated in the same manner as in Example 1, thereby obtaining a powdery gas-emitting bath additive. This additive had the same preservation stability and massothreapeutical effect as in the case of Example 1.

EXAMPLE 4

Sixty parts of sodium sesquicarbonate, 40 parts of citric acid, 0.5 part of sodium aluminate, 1 part of a perfume, and a suitable amount of a colorant were used and treated in the same manner as in Example 2, thereby obtaining a powdery gas-emitting bath additive. This additive had the same preservation stability and effect as in the case of Example 1.

EXAMPLE 5

Fifty parts of sodium hydrogencarbonate, 55 parts of citric acid, 2 parts of magnesium oxide, 1 part of a perfume, and a suitable amount of a colorant were used and treated in the same manner as in Example 1, thereby obtaining tablets of gas-emitting bath additive. The additive had the same preservation stability as in the case of Example 1. Upon charge of the tablets into a hot bath, they were found to emit gas bubbles so that the massotherapeutical effect was given to the skin while showing the blood-circulation effect. The pH of a 0.01 wt % aqueous solution of the bath additive was 5.4.

EXAMPLE 6

Thirty parts of sodium hydrogencarbonate, 40 parts of succinic acid, 25 parts of sodium sulfate, 2 parts of sodium aluminate, 1 part of a perfume, and a suitable amount of a colorant were used and treated in the same manner as in Example 1, thereby obtaining a gas-emitting bath additive in the form of tablets. This additive had the same preservation stability as that of Example 1. When the additive was charged into a hot bath, it turned into a kind of carbonate or salt cake spring. A 0.01 wt % aqueous solution of the gas-emitting bath additive had a pH of 6.5.

EXAMPLE 7

Forty parts of sodium sulfate, 30 parts of sodium hydrogencarbonate, 30 parts of sodium phosphate, 2 parts of magnesium oxide, 1 part of a perfume, and a suitable amount of a colorant were used and treated in the same manner as in Example 1, thereby obtaining tablets of gas-emitting bath additive. This additive had the same preservation stability and effect as in the case of Example 1.

EXAMPLE 8

Seventy parts of sodium hydrogencarbonate, 30 parts of fumaric acid, 2 parts of magnesium oxide, 1 part of sodium aluminate, 1 part of a perfume, a suitable amount of a colorant, and 0.5 part of sodium CMC were used and treated in the same manner as in Example 1, thereby obtaining tablets of gas-emitting bath additive. This additive had the same preservation stability and effect as in the case of Example 1.

COMPARATIVE EXAMPLE

Examples 1–7 were repeated without use of magnesium oxide or sodium aluminate, thereby obtaining gas-emitting bath additives. These additives were preserved in the same manner as in the foregoing examples, with the result that carbon dioxide gas generated in 3 days to 2 weeks and the packaging containers were each expanded considerably.

What is claimed is:
1. A bath additive composition comprising:
   (1) 5 to 80 wt % based on the total weight of the composition of dried carbonate selected from the group consisting of sodium hydrogencarbonate, sodium carbonate, sodium sesquicarbonate, potassium carbonate; potassium hydrogencarbonate and ammonium carbonate;
   (2) 10 to 300 wt %, based on ingredient (1), of a dried acid selected from the group consisting of citric acid, tartaric, malic acid, malonic acid, pyridone-carboxylic acid, succinic acid, fumaric acid, phos- phoric acid, sodium citrate, sodium succinate, sodium fumarate and sodium phosphate, and (3) 0.5 to 15 wt % based on the total weight of the composition of a stabilizer which is sodium aluminate.

2. The composition of claim 1, wherein said dried carbonate is contained in an amount of from 10-50% by weight.

3. The composition of claim 1, wherein said acid is added in an amount of from 30-150 wt. % based on the weight of said dried carbonate.

4. The composition of claim 1, wherein said acid is succinic acid or fumaric acid and is added in an amount of from 20-150% by weight.

5. The composition of claim 1, wherein said acid is sodium succinate and is added in an amount of from 40-300% by weight.

6. The composition of claim 1, wherein said acid is sodium fumarate and is added in an amount of from 30-250% by weight.

7. The composition of claim 1, wherein said stabilizer is added in an amount of from 0.5-10% by weight.

8. The composition of claim 1, which further comprises 30-500% by weight based on the total weight of the composition of one or more of $Na_2SO_4$, $MgSO_4$, $ZnSO_4$, or NaCl.

9. The composition of claim 1, which is formulated such that an aqueous solution of 0.01% of said composition has a pH of from about 5-7.

10. The composition of claim 1, which consists essentially of about 70 weight % based on the total weight of the composition of sodium carbonate, about 30 weight % based on the weight of said sodium carbonate of citric acid, and about 5 weight % based on the total weight of the composition of sodium aluminate.

11. The composition of claim 1, which consists essentially of about 60 weight % based on the total weight of the composition of sodium sesquicarbonate, about 40 weight % based on the weight of said sodium sesquicarbonate of citric acid, and about 5 weight % based on the total weight of the composition of sodium aluminate.

12. The composition of claim 1, which consists essentially of about 30 weight % based on the total weight of the composition of sodium hydrogen carbonate, about 40 weight % based on the weight of said sodium hydrogen carbonate of succinic acid, about 25 weight % based on the total weight of the composition of sodium sulfate, and about 2 weight % based on the total weight of the composition of sodium aluminate.

13. A method for exerting a massotherapeutical effect on skin, which comprises contacting skin with an aqueous solution of a composition which comprises (1) 5-80 weight percent of dried carbonate selected from the group consisting of sodium hydrogen carbonate, sodium carbonate, sodium sesquicarbonate, potassium carbonate, potassium hydrogen carbonate, and ammonium carbonate, (2) 10-300 weight percent, based on ingredient 1, of a dried acid selected from the group consisting of citric acid, tartaric acid, malic acid, malonic acid, pyridone carboxylic acid, succinic acid, fumaric acid, phosphoric acid, sodium citrate, sodium succinate, sodium fumarate and sodium phosphate, and (3) 0.5-15 weight percent of a stabilizer selected from the group consisting of magnesium oxide and sodium aluminate.

14. The method of claim 13, wherein said contacting is carried out in bath water.

* * * * *